(12) United States Patent
Efrati

(10) Patent No.: US 10,925,835 B2
(45) Date of Patent: *Feb. 23, 2021

(54) CELECOXIB AND AMLODIPINE FORMULATION AND METHOD OF MAKING THE SAME

(71) Applicants: Dexcel Ltd., Or-Akiva (IL); Kitov Pharmaceuticals, Tel Aviv (IL)

(72) Inventor: Yitshak Itsik Efrati, Modiin (IL)

(73) Assignees: DEXCEL LTD., Or-Akiva (IL); KITOV PHARMACEUTICALS, Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/006,959

(22) Filed: Aug. 31, 2020

(65) Prior Publication Data

US 2020/0390713 A1    Dec. 17, 2020

Related U.S. Application Data

(63) Continuation of application No. 16/427,499, filed on May 31, 2019, which is a continuation of application No. 16/008,538, filed on Jun. 14, 2018, now Pat. No. 10,350,171.

(60) Provisional application No. 62/529,061, filed on Jul. 6, 2017.

(51) Int. Cl.
| | | |
|---|---|---|
| A61K 9/28 | (2006.01) |
| A61K 9/20 | (2006.01) |
| A61K 9/50 | (2006.01) |
| A61K 31/415 | (2006.01) |
| A61K 47/02 | (2006.01) |
| A61K 47/10 | (2017.01) |
| A61K 47/12 | (2006.01) |
| A61K 47/26 | (2006.01) |
| A61K 47/32 | (2006.01) |
| A61K 47/38 | (2006.01) |
| A61K 47/44 | (2017.01) |
| A61K 47/18 | (2017.01) |
| A61K 31/4422 | (2006.01) |

(52) U.S. Cl.
CPC .......... *A61K 9/2077* (2013.01); *A61K 9/5084* (2013.01); *A61K 31/415* (2013.01); *A61K 47/02* (2013.01); *A61K 47/10* (2013.01); *A61K 47/12* (2013.01); *A61K 47/18* (2013.01); *A61K 47/26* (2013.01); *A61K 47/32* (2013.01); *A61K 47/38* (2013.01); *A61K 47/44* (2013.01); *A61K 31/4422* (2013.01); *A61K 2300/00* (2013.01)

(58) Field of Classification Search
CPC ...... A61K 9/16; A61K 9/1605; A61K 9/1682; A61K 9/20; A61K 9/2004; A61K 9/2013; A61K 9/2077; A61K 9/2084
See application file for complete search history.

(56) References Cited

U.S. PATENT DOCUMENTS

2002/0077328 A1 * 6/2002 Hassan .............. A61K 2300/00
514/263.31

FOREIGN PATENT DOCUMENTS

WO    WO-2014097209 A1 *  6/2014  ......... A61K 31/4422

* cited by examiner

*Primary Examiner* — Micah Paul Young
(74) *Attorney, Agent, or Firm* — W&C IP

(57) ABSTRACT

Provided herein is a celecoxib and amlodipine composition and method of making the same. The composition contains granules containing celecoxib. The amlodipine is incorporated into the composition as an extragranulate.

24 Claims, 2 Drawing Sheets

CELECOXIB AND AMLODIPINE FORMULATION AND METHOD OF MAKING THE SAME

TECHNICAL FIELD

Embodiments disclosed herein generally relate to pharmaceutical compositions of celecoxib and amlodipine and methods of making the same.

BACKGROUND

Celecoxib is a non-steroidal anti-inflammatory drug (NSAID) that has anti-inflammatory, analgesic, and anti-pyretic properties. The mechanism of action of celecoxib is believed to be due to inhibition of prostaglandin synthesis, primarily via inhibition of cyclooxygenase-2 (COX-2).

Celecoxib is indicated for the relief of signs and symptoms associated with osteoarthritis, rheumatoid arthritis, acute pain, primary dysmenorrhea, as well as the reduction of the number of adenomatous colorectal polyps in familial adenomatous polyposis as an adjunct to usual care (e.g., endoscopic surveillance, surgery). While celecoxib has been known to be effective in the treatment of the aforementioned diseases, it may also lead to adverse events including severe cardiovascular adverse reactions. Hence, celecoxib dosage forms require an FDA boxed warning on their labeling which warns physicians that this drug may cause myocardial infarctions and other cardiovascular complications, such as hypertension. It has also been established that celecoxib raises blood pressure and negates the effects of most antihypertensive drugs. Indeed, the labeling document for celecoxib warns that it may lead to hypertension, and that patients taking antihypertensives such as thiazides and diuretics may have an impaired response to these therapies.

U.S. Pat. No. 9,408,837 describes a method for ameliorating celecoxib-induced elevation of blood pressure in a subject. The method comprises a) administering at least one dose of celecoxib, wherein the at least one dose of celecoxib is sufficient to cause elevation in blood pressure in the subject; and b) administering at least one dose of amlodipine at a dosage which is sufficient to ameliorate blood pressure elevation in the subject.

US 2016/0058744 describes an oral dosage composition comprising: amlodipine or a pharmaceutically acceptable salt thereof; and celecoxib or a pharmaceutically acceptable salt thereof, wherein said amlodipine and celecoxib or pharmaceutically acceptable salts thereof are present together in a single dosage form.

There is an unmet need for single dosage forms of celecoxib and amlodipine or pharmaceutically acceptable salts thereof which are stable during manufacturing and storage.

SUMMARY

According to a first aspect, there is provided a method of preparing a pharmaceutical composition comprising celecoxib and amlodipine or pharmaceutically acceptable salts thereof, the method comprising the steps of:
(i) wet granulating celecoxib or a pharmaceutically acceptable salt thereof and one or more excipients to obtain a wet granulate;
(ii) drying the wet granulate of step (i) to obtain a dry granulate having a loss on drying (LOD) % of about 2.5% or less; and
(iii) admixing the dry granulate of step (ii) with an extragranulate comprising amlodipine or a pharmaceutically acceptable salt thereof and optionally one or more excipients.

In one embodiment, the step of wet granulating celecoxib or a pharmaceutically acceptable salt thereof and one or more excipients comprises dry mixing celecoxib or a pharmaceutically acceptable salt thereof and one or more excipients to obtain a dry mixture; and spraying the thus obtained dry mixture with a granulation solution or suspension to obtain a wet granulate.

In certain embodiments, the granulation solution or suspension comprises an aqueous medium.

In other embodiments, the granulation solution or suspension comprises an organic medium.

In some embodiments, the method of preparing a pharmaceutical composition further comprises a step of milling the dry granulate obtained in step (ii) to obtain a milled dry granulate prior to step (iii).

In various embodiments, the method of preparing a pharmaceutical composition further comprises a step of compressing the pharmaceutical composition to obtain a tablet or a caplet. Each possibility represents a separate embodiment.

In further embodiments, there is provided a pharmaceutical composition prepared by the method of the disclosure.

According to a second aspect, there is provided a pharmaceutical composition comprising:
(i) a dry granulate comprising celecoxib or a pharmaceutically acceptable salt thereof and one or more excipients, wherein the dry granulate has a loss on drying (LOD) % of about 2.5% or less; and
(ii) an extragranulate comprising amlodipine or a pharmaceutically acceptable salt thereof and optionally one or more excipients.

In one embodiment, the dry granulate has LOD % in the range of from about 0.5% to about 2.5%. In another embodiment, the dry granulate has LOD % in the range of from about 0.5% to about 2%. In yet another embodiment, the dry granulate has LOD % in the range of from about 0.5% to about 1.5%. In further embodiments, the dry granulate has LOD % in the range of from about 0.5% to about 1%. In particular embodiments, the dry granulate has LOD % of about 0.7%.

In some embodiments, the one or more excipients in the dry granulate and the one or more excipients in the extragranulate are the same or different selected from the group consisting of a diluent, a disintegrant, a surfactant, a binder, a glidant, a lubricant, and combinations thereof. Each possibility represents a separate embodiment.

In certain embodiments, the diluent comprises at least one of lactose, sucrose, mannitol, sorbitol, calcium phosphate, cellulose, kaolin, sodium chloride, and starch. Each possibility represents a separate embodiment. In one embodiment, the diluent in the extragranulate is the same as the diluent in the dry granulate, preferably wherein the diluent is mannitol.

In various embodiments, the disintegrant comprises at least one of cross-linked sodium carboxymethyl cellulose (croscarmellose sodium), cross-linked polyvinylpyrrolidone (crospovidone), sodium starch glycolate, pregelatinized starch, calcium carboxymethyl cellulose, low substituted hydroxypropyl cellulose, and magnesium aluminum silicate. Each possibility represents a separate embodiment. In one embodiment, the disintegrant in the extragranulate is the same as the disintegrant in the dry granulate, preferably wherein the disintegrant is croscarmellose sodium.

In additional embodiments, the surfactant comprises at least one of stearyl triethanolamine, sodium lauryl sulfate, sodium taurocholate, laurylaminopropionic acid, lecithin, benzalkonium chloride, benzethonium chloride, glycerin monostearate, and polyvinyl alcohol. Each possibility represents a separate embodiment. In one embodiment, the surfactant in the dry granulate is sodium lauryl sulfate.

In further embodiments, the binder comprises at least one of polyvinylpyrrolidone (povidone; PVP), hydroxypropyl cellulose (HPC), hydroxypropylmethyl cellulose (HPMC), sodium alginate, alginic acid, guar gum, acacia gum, xanthan gum, carbopol, carboxymethyl cellulose, ethyl cellulose, maltodextrin, vinylpyrrolidone/vinyl acetate copolymer, microcrystalline cellulose, starch, and methyl cellulose. Each possibility represents a separate embodiment. In one embodiment, the binder in the dry granulate is polyvinylpyrrolidone.

In some embodiments, the glidant comprises at least one of corn starch, colloidal silicon dioxide, silica anhydrous, and talc. Each possibility represents a separate embodiment. In one embodiment, the glidant in the extragranulate is colloidal silicon dioxide.

In other embodiments, the lubricant comprises at least one of magnesium stearate, calcium stearate, oleic acid, caprylic acid, stearic acid, magnesium isovalerate, calcium laurate, magnesium palmitate, behenic acid, glyceryl behenate, glyceryl stearate, sodium stearyl fumarate, potassium stearyl fumarate, zinc stearate, sodium oleate, sodium stearate, sodium benzoate, sodium acetate, sodium chloride, talc, polyethylene glycol, and hydrogenated vegetable oil. Each possibility represents a separate embodiment. In one embodiment, the lubricant in the extragranulate is magnesium stearate.

In certain embodiments, the pharmaceutical composition is in the form of a tablet, a caplet, or a capsule. Each possibility represents a separate embodiment.

In particular embodiments, the pharmaceutical composition comprises 200 mg celecoxib and 2.5, 5, or 10 mg amlodipine as active ingredients. Each possibility represents a separate embodiment.

In some embodiments, the pharmaceutically acceptable salt of amlodipine is amlodipine besylate.

In particular embodiments, the pharmaceutical composition comprises a dry granulate comprising celecoxib, a diluent, a disintegrant, a binder, and a surfactant; and an extragranulate comprising amlodipine besylate, a diluent, a disintegrant, a glidant, and a lubricant.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION

Figure 1A:
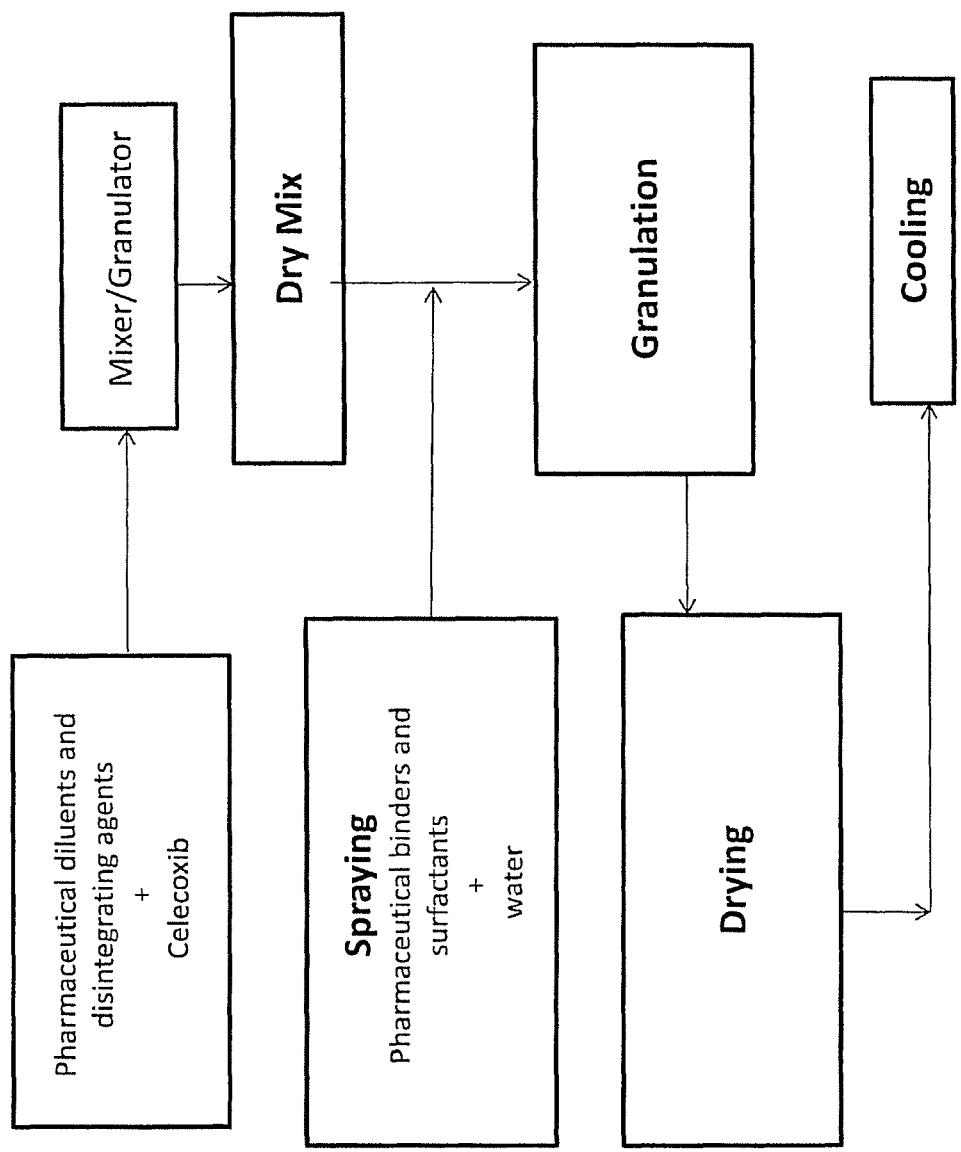
FIG. 1A-B. Flow chart of exemplary method to produce a pharmaceutical composition according to certain embodiments of the disclosure.

A pharmaceutical composition of celecoxib and amlodipine and method for preparing the same is provided herein.

Celecoxib, or 4-[5-(4-methylphenyl)-3-(trifluoromethyl)-1H-pyrazol-1-yl]benzenesulfonamide, is an FDA approved and commercially available COX-2 inhibitor. It is a non-steroidal anti-inflammatory drug (NSAID) marketed under the names Celebrex® and Celebra® and used for the treatment of pain and pain-related disorders. Celecoxib is known to be characterized by relatively poor flowability. Typically, compositions comprising celecoxib are prepared using wet granulation processes.

As used herein, "celecoxib" may also refer to a pharmaceutically acceptable salt thereof, such as, but not limited to, a base addition salt. Suitable pharmaceutically acceptable base addition salts of celecoxib include, but are not limited to, metallic salts of sodium, calcium, lithium, magnesium, potassium, strontium, aluminum and zinc; and ammonium salts derived from ammonia, primary, secondary, tertiary and quaternary amines, non-limiting examples of which are trimethylamine, cyclohexylamine, benzylamine, dibenzylamine, 2-hydroxyethylamine, bis(2-hydroxyethyl)amine, phenylethylbenzylamine, dibenzylethylenediamine, procaine, chloroprocaine, quinine, choline, and N-methylglucosamine. Each possibility represents a separate embodiment. Salts with amino acids such as glycine, ornithine, histidine, phenylglycine, lysine, and arginine are contemplated as well. Each possibility represents a separate embodiment.

Typical amounts of celecoxib in the composition are in the range of about 30% to about 70%, preferably about 40% to about 60% W/W % of the entire composition, including each integer within the specified range.

Amlodipine, or 3-ethyl-5-methyl (±)-2-[(2-aminoethoxy)methyl]-4-(2-chlorophenyl)-1,4-dihydro-6-methyl-3,5-pyridinedicarboxylate, is an angioselective calcium channel blocker used to treat high blood pressure and coronary artery disease. It is marketed in its besylate salt form under the name Norvasc®, among others. Amlodipine is known to be sensitive to moisture which leads to amlodipine degradation via a catalytic oxidative process and the production of impurities (WO 2008/062435).

As used herein, "amlodipine" may also refer to a pharmaceutically acceptable salt thereof, such as, but not limited to, sulfonate and acid addition salts. Pharmaceutically acceptable sulfonate salts include, but are not limited to, benzene sulfonate (besylate), toluene sulfonate (tosylate), and methane sulfonate (mesylate). Each possibility represents a separate embodiment. Pharmaceutically acceptable acid addition salts include, but are not limited to, salts derived from inorganic acids such as, hydrochloric, nitric, phosphoric, sulfuric, hydrobromic, hydroiodic, and the like, as well as salts derived from organic acids such as aliphatic mono- and dicarboxylic acids, phenyl-substituted alkanoic acids, hydroxy alkanoic acids, alkanedioic acids, aromatic acids, aliphatic and aromatic sulfonic acids and the like. Each possibility represents a separate embodiment. Suitable salts thus include, but are not limited to, sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, salicylate, mandelate, benzoate, chlorobenzoate, methylbenzoate, dinitrobenzoate, phthalate, benzenesulfonate, toluenesulfonate, phenylacetate, citrate, lactate, maleate, tartrate, and the like. Each possibility represents a separate embodiment. Also contemplated are salts of amino acids such as arginate and the like and gluconate or galacturonate. Each possibility represents a separate embodiment. Currently preferred is the benzene sulfonate or monobenzene sulfonate (besylate) salt of amlodipine.

Typical amounts of amlodipine in the composition are in the range of about 0.01% to about 10%, preferably about 0.1% to about 7% W/W % of the entire composition, including each integer within the specified range.

As used herein, celecoxib and/or amlodipine may also include polymorphs of celecoxib and/or amlodipine or solvates thereof. The term "polymorph" refers to a particular crystalline or amorphous solid state form of a substance, which can be characterized by particular physical properties such as X-ray diffraction, electron diffraction, IR spectra, Raman spectra, melting point, and the like.

As used herein, celecoxib and/or amlodipine may also include solvates, isomers, isomorphs, pseudopolymorphs, and prodrugs thereof, with each possibility representing a separate embodiment.

Antihypertensive drugs, such as calcium channel blockers or beta blockers, e.g. amlodipine, can be used to reduce (i.e., ameliorate) drug-induced blood pressure increases in patients that receive therapies that include the administration of stimulants or NSAIDs, e.g. celecoxib. This therapy, which counteracts iatrogenic therapies that result in elevated blood pressure, reduces the risk of serious cardiovascular complications, including heart attack, stroke, and death in these patients. To ameliorate elevations in blood pressure via the adjunctive use of at least one antihypertensive drug, the antihypertensive drug should be administered at the same time as the stimulants or NSAIDs (U.S. Pat. No. 9,408,837).

Provided herein is a pharmaceutical composition of celecoxib and amlodipine. The composition enables the administration of amlodipine and celecoxib simultaneously in a single dosage form.

It was not previously realized that a stable composition of celecoxib and amlodipine can be obtained by first preparing a granulate of celecoxib via wet granulation, followed by drying the wet granulate, and admixing the dry granulate with amlodipine as an extragranulate. The composition exerts advantageous properties including stability during manufacturing and storage. According to the principles provided herein, celecoxib can be prepared as a wet granulate having desirable flowability. Following its formation, the wet granulate is dried, thereby enabling its admixture with the moisture-sensitive amlodipine to afford a stable composition.

According to certain aspects and embodiments, there is provided a method for preparing a composition comprising celecoxib and amlodipine, the method comprises wet granulating celecoxib and one or more pharmaceutically acceptable excipients to obtain a wet granulate. The thus obtained wet granulate is subsequently dried to obtain a dry granulate. Finally, the dry granulate is admixed with an extragranulate comprising amlodipine and optionally one or more pharmaceutically acceptable excipients.

Wet granulation of celecoxib and one or more pharmaceutically acceptable excipients can be performed in a mixer/granulator (e.g. using a V-processor) as is known in the art. In certain embodiments, wet granulation is performed by dry mixing celecoxib with one or more pharmaceutically acceptable excipients to obtain a dry mixture, followed by spraying the dry mixture with a granulation solution or suspension to obtain a wet granulate. In one embodiment, the granulation solution or suspension comprises an aqueous medium, i.e. water, optionally further comprising at least one of a binder, a surfactant, a tonicity enhancing agent and the like, to facilitate the formation of the wet granulate. In yet other embodiments, the granulation solution or suspension comprises an organic medium, including, but not limited to, protic or aprotic solvents, optionally admixed with water, e.g. isopropyl alcohol and water or acetone and water and the like. Each possibility represents a separate embodiment.

In certain embodiments, the step of drying the wet granulate of celecoxib is obtained by heating the granulate to a temperature above room temperature and maintaining the elevated temperature, typically for several hours until the LOD % of the granulate reaches a desired value. The drying temperature, and thus the drying duration, can be varied in order to achieve the desired moisture content. The wet granulate may be dried at a temperature of about 30° C. to about 90° C., including each integer within the specified range. In other embodiments, the wet granulate may be dried at a temperature of about 40° C. to about 80° C., including each integer within the specified range. In yet other embodiments, the wet granulate may be dried at a temperature of about 50° C. to about 70° C., including each integer within the specified range. In specific embodiments, the wet granulate may be dried at a temperature of about 60° C. The drying duration may be in the range of about 1 hour to about 10 hours, including each integer within the specified range. For example, the drying duration may be in the range of about 6 hours to about 10 hours, including each integer within the specified range. In specific embodiments, the drying duration is about 8 hours.

According to the principles provided herein, the LOD % of the dry granulate is about 2.5% or less. In certain embodiments, the LOD % of the dry granulate is in the range of about 0.5% to about 2%. In other embodiments, the LOD % of the dry granulate is in the range of about 0.5% to about 1.5%, for example about 0.5% to about 1%, about 0.5% to about 0.9%, about 0.6% to about 0.8%, or about 0.7%. Each possibility represents a separate embodiment. In various embodiments, the drying temperature is about 60° C. and the drying duration is about 8 hours.

As used herein, "loss on drying" or "LOD" % can be measured by any of the many suitable means which are well known to those of skill in the art, including, but not limited to, Karl Fischer titration. Suitable measuring devices include, but not limited to, CENCO moisture balance, CSC digital moisture balance, Praxis moisture balance, HR-73 moisture analyzer (Mettler Toledo) etc.

In some embodiments, the method of preparing a composition comprising celecoxib and amlodipine further comprises a step of cooling the dried granulate after the drying step, for example to room temperature or slightly above room temperature. Typically room temperature refers to 25±5° C.

In certain embodiments, the dry granulate may further be milled to produce a milled dry granulate. Typically, milling is performed to obtain a mean particle size of the dry granulate of about 2,000 microns or less, for example from about 50 microns to about 2,000 microns, including each integer within the specified range. In certain embodiments, at least about 50% of the dry granules have a particle size of less than about 1,000 microns, for example about 100 microns to about 1,000 microns, including each integer within the specified range. Preferably at least about 50% of the dry granules have a particle size of less than about 850 microns, for example about 100 microns to about 850 microns, including each integer within the specified range. The equipment used to mill the granules may include for example, fluid energy milling, impact milling, cutting milling, compression milling, screening milling, tumbling milling, calibrating milling, and oscillating milling. Each possibility represents a separate embodiment.

In further embodiments, sieving of the granules or the milled granules may also be performed as is known in the art, for example using vibrators or shakers.

Following drying of the granulate, amlodipine is admixed as an extragranulate, optionally with one or more excipients. The admixing of amlodipine and the optional excipient(s) may be performed using any suitable type of mixer or blender. Non-limiting examples include simple paddle mixer, ribbon and/or tumbling mixers, plow blenders and drum agglomerators, V-blenders, double cone blenders, slant cone blenders, twin shell blenders, e.g., PATTERSON KELLEY V Blenders, GEMCO double cone blenders, diffusion blender and the like among others. Each possibility represents a separate embodiment.

According to the principles provided herein, the composition of the disclosure contains one or more pharmaceutically acceptable excipients. It is contemplated that the one or more pharmaceutically acceptable excipients are present in the celecoxib granulate and/or admixed together with amlodipine as an extragranulate. It will be recognized by one of skill in the art that the one or more pharmaceutically acceptable excipients in the dry granulate and the one or more pharmaceutically acceptable excipients in the extragranulate are the same or different with each possibility representing a separate embodiment. Suitable pharmaceutically acceptable excipients include, but not limited to, a diluent, a disintegrant, a surfactant, a binder, a glidant, a lubricant and combinations thereof. Each possibility represents a separate embodiment.

Suitable diluents include, but are not limited to, lactose, sucrose, mannitol, sorbitol, calcium phosphate, cellulose, kaolin, sodium chloride, and starch. Each possibility represents a separate embodiment. Typical amounts of diluent in the dry granulate are in the range of about 5% to about 35%, preferably about 10% to about 30% W/W % of the entire composition, including each integer within the specified range. In some embodiments, the weight percent ratio of celecoxib to diluent in the dry granulate is from about 4:1 to about 1:1, including all iterations of ratios within the specified range. In other embodiments, the weight percent ratio of celecoxib to diluent in the dry granulate is from about 3:1 to about 1:1, including all iterations of ratios within the specified range. In yet other embodiments, the weight percent ratio of celecoxib to diluent in the dry granulate is from about 3:1 to about 2:1, including all iterations of ratios within the specified range. Typical amounts of diluent in the extragranulate are in the range of about 5% to about 20%, preferably about 9% to about 15% W/W % of the entire composition, including each integer within the specified range. In some embodiments, the weight percent ratio of amlodipine to diluent in the extragranulate is from about 1:2 to about 1:25, including all iterations of ratios within the specified range. In other embodiments, the weight percent ratio of amlodipine to diluent in the extragranulate is from about 1:2 to about 1:20, including all iterations of ratios within the specified range. In yet other embodiments, the weight percent ratio of amlodipine to diluent in the extragranulate is from about 1:3 to about 1:20, including all iterations of ratios within the specified range. In specific embodiments, the diluent in the extragranulate is the same as the diluent in the dry granulate, preferably wherein the diluent is mannitol.

Suitable disintegrants include, but are not limited to, cross-linked sodium carboxy methyl cellulose (croscarmellose sodium), cross-linked polyvinylpyrrolidone (crospovidone), sodium starch glycolate, pregelatinized starch, calcium carboxymethyl cellulose, low substituted hydroxypropyl cellulose, and magnesium aluminum silicate. Each possibility represents a separate embodiment. Typical amounts of disintegrant in the dry granulate are in the range of about 1% to about 10%, preferably about 2% to about 8%, W/W % of the entire composition, including each integer within the specified range. In some embodiments, the weight percent ratio of celecoxib to disintegrant in the dry granulate is from about 20:1 to about 5:1, including all iterations of ratios within the specified range. In other embodiments, the weight percent ratio of celecoxib to disintegrant in the dry granulate is from about 15:1 to about 5:1, including all iterations of ratios within the specified range. In yet other embodiments, the weight percent ratio of celecoxib to disintegrant in the dry granulate is from about 15:1 to about 10:1, including all iterations of ratios within the specified range. Typical amounts of disintegrant in the extragranulate are in the range of about 0.2% to about 10%, preferably about 0.5% to about 5%, W/W % of the entire composition, including each integer within the specified range. In some embodiments, the weight percent ratio of amlodipine to disintegrant in the extragranulate is from about 4:1 to about 1:4, including all iterations of ratios within the specified range. In other embodiments, the weight percent ratio of amlodipine to disintegrant in the extragranulate is from about 3:1 to about 1:4, including all iterations of ratios within the specified range. In yet other embodiments, the weight percent ratio of amlodipine to disintegrant in the extragranulate is from about 2:1 to about 1:4, including all iterations of ratios within the specified range. In specific embodiments, the disintegrant in the extragranulate is the same as the disintegrant in the dry granulate, preferably wherein the disintegrant is croscarmellose sodium.

Suitable surfactants include, but are not limited to, stearyl triethanolamine, sodium lauryl sulfate, sodium taurocholate, laurylaminopropionic acid, lecithin, benzalkonium chloride, benzethonium chloride, glycerin monostearate, and polyvinyl alcohol. Each possibility represents a separate embodiment. Typical amounts of surfactant in the dry granulate are in the range of about 0.5% to about 10%, preferably about 1% to about 6%, W/W % of the entire composition, including each integer within the specified range. In some embodiments, the weight percent ratio of celecoxib to surfactant in the dry granulate is from about 30:1 to about 10:1, including all iterations of ratios within the specified range. In other embodiments, the weight percent ratio of celecoxib to surfactant in the dry granulate is from about 25:1 to about 10:1, including all iterations of ratios within the specified range. In yet other embodiments, the weight percent ratio of celecoxib to surfactant in the dry granulate is from about 25:1 to about 15:1, including all iterations of ratios within the specified range. In specific embodiments, the surfactant in the dry granulate is sodium lauryl sulfate.

Suitable binders include, but are not limited to, polyvinylpyrrolidone (povidone; PVP), hydroxypropyl cellulose (HPC), hydroxypropylmethyl cellulose (HPMC), sodium alginate, alginic acid, guar gum, acacia gum, xanthan gum, carbopol, carboxymethyl cellulose, ethyl cellulose, maltodextrin, vinylpyrrolidone/vinyl acetate copolymer, microcrystalline cellulose, starch, and methyl cellulose. Each possibility represents a separate embodiment. Typical amounts of binder in the dry granulate are in the range of about 0.5% to about 10%, preferably about 1% to about 6%, W/W % of the entire composition, including each integer within the specified range. In some embodiments, the weight percent ratio of celecoxib to binder in the dry granulate is from about 30:1 to about 5:1, including all iterations of ratios within the specified range. In other embodiments, the weight percent ratio of celecoxib to binder in the dry granulate is from about 25:1 to about 5:1, including all iterations of ratios within the specified range. In yet other embodiments, the weight percent ratio of celecoxib to binder in the dry granulate is from about 20:1 to about 10:1, including all iterations of ratios within the specified range. In specific embodiments, the binder in the dry granulate is polyvinylpyrrolidone.

Suitable glidants include, but are not limited to, corn starch, colloidal silicon dioxide, silica anhydrous, and talc. Each possibility represents a separate embodiment. Typical amounts of glidant in the extragranulate are in the range of about 0.1% to about 5%, preferably about 0.2% to about 3%, W/W % of the entire composition, including each integer within the specified range. In some embodiments, the weight percent ratio of amlodipine to glidant in the extragranulate is from about 1:1 to about 20:1, including all iterations of ratios within the specified range. In other embodiments, the weight percent ratio of amlodipine to glidant in the extragranulate is from about 1:1 to about 15:1, including all iterations of ratios within the specified range. In yet other embodiments, the weight percent ratio of amlodipine to glidant in the extragranulate is from about 1:1 to about 10:1, including all iterations of ratios within the specified range. In specific embodiments, the glidant in the extragranulate is colloidal silicon dioxide.

Suitable lubricants include, but are not limited to, magnesium stearate, calcium stearate, oleic acid, caprylic acid, stearic acid, magnesium isovalerate, calcium laurate, magnesium palmitate, behenic acid, glyceryl behenate, glyceryl stearate, sodium stearyl fumarate, potassium stearyl fumarate, zinc stearate, sodium oleate, sodium stearate, sodium benzoate, sodium acetate, sodium chloride, talc, polyethylene glycol, and hydrogenated vegetable oil. Each possibility represents a separate embodiment. Typical amounts of lubricant in the extragranulate are in the range of about 0.1% to about 5%, preferably about 0.5% to about 3%, W/W % of the entire composition, including each integer within the specified range. In some embodiments, the weight percent ratio of amlodipine to lubricant in the extragranulate is from about 10:1 to about 1:10, including all iterations of ratios within the specified range. In other embodiments, the weight percent ratio of amlodipine to lubricant in the extragranulate is from about 5:1 to about 1:5, including all iterations of ratios within the specified range. In yet other embodiments, the weight percent ratio of amlodipine to lubricant in the extragranulate is from about 5:1 to about 1:3, including all iterations of ratios within the specified range. In specific embodiments, the lubricant in the extragranulate is magnesium stearate.

It is contemplated that other pharmaceutically acceptable excipients, which may be intra-granular excipients, extra-granular excipients, or a combination thereof, may be incorporated in the composition of the disclosure. Suitable excipients may include, but are not limited to a filler, an anti-tacking agent, a plasticizer, a tonicity enhancing agent, a wetting agent, a buffering substance, a colorant, a preservative, and any combination thereof.

Non-limiting examples of suitable fillers include sugars (such as lactose, glucose, fructose, or sucrose), microcrystalline cellulose, dicalcium phosphate, a sugar alcohol (such as sorbitol, mannitol, maltitol, lactitol, xylitol, isomalt, and erythritol), a hydrogenated starch hydrolysate, a starch (such as corn starch, or potato starch), or sodium carboxymethyl cellulose, ethyl cellulose, cellulose acetate, and any combination thereof. Each possibility represents a separate embodiment.

Non-limiting examples of anti-tacking agents include talc, magnesium stearate, calcium stearate, stearic acid, colloidal silicon dioxide, and the like among others. Each possibility represents a separate embodiment.

Non-limiting examples of plasticizers include dibutyl sebacate, polyethylene glycol, polypropylene glycol, dibutyl phthalate, diethyl phthalate, triethyl citrate, tributyl citrate, acetylated monoglyceride, acetyl tributyl citrate, triacetin, dimethyl phthalate, benzyl benzoate, butyl and/or glycol esters of fatty acids, refined mineral oils, oleic acid, castor oil, corn oil, camphor, glycerol, and sorbitol among others. Each possibility represents a separate embodiment.

Non-limiting examples of tonicity enhancing agents include ionic and non-ionic compounds. Each possibility represents a separate embodiment. For example, ionic compounds include, but are not limited to, alkali metal or alkaline earth metal halides, such as, for example, $CaCl_2$) KBr, KCl, LiCl, NaI, NaBr, NaCl, or boric acid. Each possibility represents a separate embodiment. Non-ionic compounds include, but are not limited to, urea, glycerol, sorbitol, mannitol, propylene glycol, and dextrose. Each possibility represents a separate embodiment.

Non-limiting examples of wetting agents include glycerin, starches, and the like. Each possibility represents a separate embodiment.

Non-limiting examples of buffering substances include acidic buffering agents such as short chain fatty acids, citric acid, acetic acid, hydrochloric acid, sulfuric acid, and fumaric acid, with each possibility representing a separate embodiment; and basic buffering agents such as tris, sodium carbonate, sodium bicarbonate, sodium hydroxide, potassium hydroxide, and magnesium hydroxide, with each possibility representing a separate embodiment.

Non-limiting examples of colorants include alumina (dried aluminum hydroxide), annatto extract, calcium carbonate, canthaxanthin, caramel, β-carotene, cochineal extract, carmine, potassium sodium copper chlorophyllin (chlorophyllin-copper complex), dihydroxyacetone, bismuth oxychloride, synthetic iron oxide, ferric ammonium ferrocyanide, ferric ferrocyanide, chromium hydroxide green, chromium oxide greens, guanine, mica-based pearlescent pigments, pyrophyllite, mica, dentifrices, talc, titanium dioxide, aluminum powder, bronze powder, copper powder, and zinc oxide. Each possibility represents a separate embodiment.

Non-limiting examples of preservatives include quaternary ammonium salts such as benzalkonium chloride, benzoxonium chloride or polymeric quaternary ammonium salts, alkyl-mercury salts of thiosalicylic acid, such as, for example, thiomersal, phenylmercuric nitrate, phenylmercuric acetate or phenylmercuric borate, parabens, such as, for example, methylparaben or propylparaben, alcohols, such as, for example, chlorobutanol, benzyl alcohol or phenyl ethanol, guanidine derivatives, such as, for example, chlorohexidine or polyhexamethylene biguanide, sorbic acid or ascorbic acid. Each possibility represents a separate embodiment.

According to certain aspects and embodiments, the pharmaceutical composition of the disclosure comprises a dry granulate comprising celecoxib, a diluent, a disintegrant, a binder, and a surfactant; and an extragranulate comprising amlodipine besylate, a diluent, a disintegrant, a glidant, and a lubricant. In some embodiments, the pharmaceutical composition of the disclosure comprises a dry granulate comprising about 40% to about 60% celecoxib, about 10% to about 30% diluent, about 2% to about 8% disintegrant, about 1% to about 6% binder, and about 1% to about 6% surfactant; and an extragranulate comprising about 0.1% to about 7% amlodipine besylate, about 9% to about 15% diluent, about 0.5% to about 5% disintegrant, about 0.2% to about 3% glidant, and about 0.5% to about 3% lubricant, % weight of the total composition. In additional embodiments, the pharmaceutical composition of the disclosure comprises a dry granulate comprising celecoxib, mannitol, croscarmellose sodium, polyvinylpyrrolidone, and sodium lauryl sulfate; and an extragranulate comprising amlodipine besylate, mannitol, croscarmellose sodium, colloidal silicon dioxide, and magnesium stearate.

The pharmaceutical composition disclosed herein may be administered by any of the many suitable means which are well known to those of skill in the art. Preferably, the mode of administration is oral. The composition may be in any form suitable for oral administration, including, but not limited to, a tablet, a caplet, powder or granules encapsulated in capsules (e.g. soft or hard gelatin capsules), cachets or any sprinkle dosage form. Each possibility represents a separate embodiment.

In certain embodiments, the composition may be compressed to a tablet or a caplet. In accordance with these embodiments, the method of preparing the pharmaceutical composition may further comprise a step of compression. Suitable compression equipment includes, but is not limited to, mini press, single or double punch or rotary tablet press such as Killian, Korsch, Colton, Manesty, Stokes, Vector, and the like among others. Each possibility represents a separate embodiment. In some embodiments, the tablet or caplet is compressed using a compression force that affords a target hardness of about 40 N to about 150 N, including each integer within the specified range. Typical hardness values include, for example, about 50 N to about 130 N, preferably about 70 N to about 125 N, including each integer within the specified range. In certain embodiments, the tablet is further characterized by having friability of about 1% or less, for example about 0.2% to about 1%.

The composition disclosed herein is useful as anti-inflammatory, analgesic, and antipyretic while affording control over blood pressure thereby reducing the risk of cardiovascular complications including, but not limited to, heart attack, stroke, and even death. The composition is primarily directed to a mammal, preferably a human. The amount of a composition to be administered depends on various factors including, but not limited to, the subject being treated (age and gender) and the severity of the disease being treated, and can be determined by the judgment of the prescribing physician. Because of patient-to-patient variability, dosages are a guideline only and the physician may adjust doses of the compounds to achieve the level of effective treatment that the physician considers appropriate for the patient. In considering the degree of treatment desired, the physician must balance a variety of factors such as, but not limited to, the age of the patient and the presence of other diseases or conditions. The compositions disclosed herein may contain any dosage of the celecoxib or amlodipine active pharmaceutical ingredients. The celecoxib dose is generally in the range of from about 100 mg to about 400 mg, or in the range of from about 150 mg to about 250 mg, or preferably about 200 mg. The amlodipine dose is generally in the range of from about 0.1 mg to about 25 mg, or in the range of from about 1 mg to about 15 mg. In preferred embodiments, the amlodipine dose is about 2.5 mg, about 5 mg, or about 10 mg. Each possibility represents a separate embodiment.

The term "therapeutically effective amount" or "an effective amount" as used herein refers to a quantity of a compound which is sufficient to provide a beneficial effect to the subject to which the compound is administered. The effective amount can be determined by any one of ordinary skill in the art and can be tested on various models both in vitro and in vivo.

As used herein and in the appended claims, the term "about" refers to ±10%.

As used herein and in the appended claims, the singular forms "a", "an", and "the" include plural references unless the context clearly dictates otherwise. It should be noted that the term "and" or the term "or" are generally employed in its sense including "and/or" unless the context clearly dictates otherwise.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1

Exemplary manufacture of a composition containing celecoxib and amlodipine according to certain embodiments of the disclosure.

Purified water, a binder (e.g. polyvinylpyrrolidone), and a surfactant (e.g. sodium lauryl sulfate) were mixed until fully dissolved to produce the granulation solution. A disintegrant (e.g. croscarmellose sodium), celecoxib, and optionally a diluent (e.g. mannitol) were mixed as a dry blend.

Figure 1B:
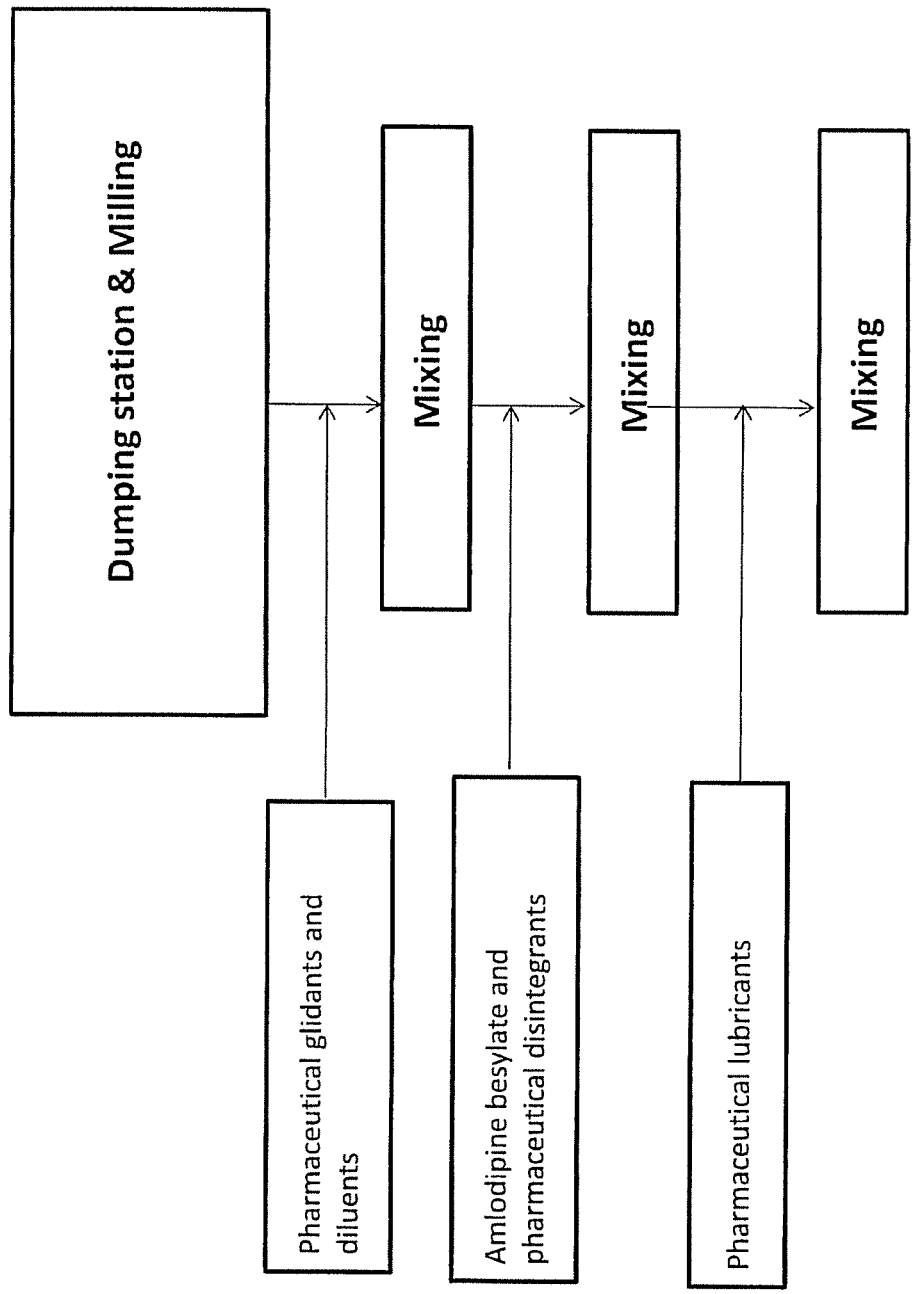

The granulation solution was sprayed onto the dry blend to form a wet granulate. The wet granulate was subsequently dried at a temperature of about 60° C. for several hours until LOD % of 0.5-2.5% was reached. The dry granulate was then cooled with the aid of flowing cool water in the casing. The dry granulate was milled and sieved followed by the admixing with amlodipine besylate, a disintegrant (e.g. croscarmellose sodium), a diluent (e.g. mannitol), and a glidant (e.g. colloidal silicon dioxide). A lubricant (e.g. magnesium stearate) was then added. A flowchart of the aforementioned process of manufacturing is shown in FIG. 1A-B. The composition was further compressed using Korsch XL.

Exemplary compositions within the scope of the present disclosure are outlined in Tables 1-13. The thickness, friability, and hardness results of these exemplary compositions after compression are shown in Table 14.

TABLE 1

| Substance | mg/tab |
| --- | --- |
| Granulate | |
| Celecoxib | 200.00 |
| Mannitol | 80.75 |
| Croscarmellose sodium | 16.00 |
| Polyvinylpyrrolidone | 20.00 |
| Sodium lauryl sulfate | 11.00 |
| Extra-granulate | |
| Amlodipine besylate | 13.87 |
| Mannitol | 44.38 |
| Croscarmellose sodium | 8.00 |

TABLE 1-continued

| Substance | mg/tab |
|---|---|
| Colloidal silicon dioxide | 2.00 |
| Magnesium stearate | 4.00 |
| Total | 400.00 |

TABLE 2

| Substance | mg/tab |
|---|---|
| Granulate | |
| Celecoxib | 200.00 |
| Mannitol | 88.76 |
| Croscarmellose sodium | 16.00 |
| Polyvinylpyrrolidone | 12.00 |
| Sodium lauryl sulfate | 11.00 |
| Extra-granulate | |
| Amlodipine besylate | 13.87 |
| Mannitol | 44.37 |
| Croscarmellose sodium | 8.00 |
| Colloidal silicon dioxide | 2.00 |
| Magnesium stearate | 4.00 |
| Total | 400.00 |

TABLE 3

| Substance | mg/tab |
|---|---|
| Granulate | |
| Celecoxib | 200.00 |
| Mannitol | 39.10 |
| Microcrystalline cellulose | 94.00 |
| Croscarmellose sodium | 16.00 |
| Polyvinylpyrrolidone | 12.00 |
| Sodium lauryl sulfate | 11.00 |
| Extra-granulate | |
| Amlodipine besylate | 13.9 |
| Croscarmellose sodium | 8.00 |
| Colloidal silicon dioxide | 2.00 |
| Magnesium stearate | 4.00 |
| Total | 400.00 |

TABLE 4

| Substance | mg/tab |
|---|---|
| Granulate | |
| Celecoxib | 200.00 |
| Mannitol | 92.75 |
| Croscarmellose sodium | 12.00 |
| Polyvinylpyrrolidone | 12.00 |
| Sodium lauryl sulfate | 11.00 |
| Extra-granulate | |
| Amlodipine besylate | 13.87 |
| Mannitol | 44.38 |
| Croscarmellose sodium | 8.00 |
| Colloidal silicon dioxide | 2.00 |
| Magnesium stearate | 4.00 |
| Total | 400.00 |

TABLE 5

| Substance | mg/tab |
|---|---|
| Granulate | |
| Celecoxib | 200.00 |
| Mannitol | 96.75 |
| Croscarmellose sodium | 8.00 |
| Polyvinylpyrrolidone | 12.00 |
| Sodium lauryl sulfate | 11.00 |
| Extra-granulate | |
| Amlodipine besylate | 13.87 |
| Mannitol | 48.38 |
| Croscarmellose sodium | 4.00 |
| Colloidal silicon dioxide | 2.00 |
| Magnesium stearate | 4.00 |
| Total | 400.00 |

TABLE 6

| Substance | mg/tab |
|---|---|
| Granulate | |
| Celecoxib | 200.00 |
| Mannitol | 96.75 |
| Croscarmellose sodium | 16.00 |
| Polyvinylpyrrolidone | 4.00 |
| Sodium lauryl sulfate | 11.00 |
| Extra-granulate | |
| Amlodipine besylate | 13.87 |
| Mannitol | 44.37 |
| Croscarmellose sodium | 8.00 |
| Colloidal silicon dioxide | 2.00 |
| Magnesium stearate | 4.00 |
| Total | 400.00 |

TABLE 7

| Substance | mg/tab |
|---|---|
| Granulate | |
| Celecoxib | 200.00 |
| Mannitol | 137.10 |
| Croscarmellose sodium | 16.00 |
| Polyvinylpyrrolidone | 11.50 |
| Sodium lauryl sulfate | 7.50 |
| Extra-granulate | |
| Amlodipine besylate | 13.90 |
| Croscarmellose sodium | 8.00 |
| Colloidal silicon dioxide | 2.00 |
| Magnesium stearate | 4.00 |
| Total | 400.00 |

TABLE 8

| Substance | mg/tab |
|---|---|
| Granulate | |
| Celecoxib | 200.00 |
| Mannitol | 90.42 |
| Croscarmellose sodium | 16.00 |
| Polyvinylpyrrolidone | 11.50 |
| Sodium lauryl sulfate | 9.00 |
| Extra-granulate | |

TABLE 8-continued

| Substance | mg/tab |
|---|---|
| Amlodipine besylate | 13.87 |
| Mannitol | 45.21 |
| Croscarmellose sodium | 8.00 |
| Colloidal silicon dioxide | 2.00 |
| Magnesium stearate | 4.00 |
| Total | 400.00 |

TABLE 9

| Substance | mg/tab |
|---|---|
| Granulate | |
| Celecoxib | 200.00 |
| Mannitol | 199.10 |
| Croscarmellose sodium | 19.33 |
| Polyvinylpyrrolidone | 14.00 |
| Sodium lauryl sulfate | 15.00 |
| Extra-granulate | |
| Amlodipine besylate | 13.87 |
| Croscarmellose sodium | 9.66 |
| Colloidal silicon dioxide | 4.00 |
| Magnesium stearate | 5.00 |
| Total | 479.96 |

TABLE 10

| Substance | mg/tab |
|---|---|
| Granulate | |
| Celecoxib | 200.00 |
| Mannitol | 200.00 |
| Croscarmellose sodium | 19.34 |
| Polyvinylpyrrolidone | 14.00 |
| Sodium lauryl sulfate | 14.10 |
| Extra-granulate | |
| Amlodipine besylate | 13.90 |
| Croscarmellose sodium | 9.66 |
| Colloidal silicon dioxide | 4.00 |
| Magnesium stearate | 5.00 |
| Total | 480.00 |

TABLE 11

| Substance | mg/tab |
|---|---|
| Granulate | |
| Celecoxib | 200.00 |
| Mannitol | 179.80 |
| Croscarmellose sodium | 18.00 |
| Polyvinylpyrrolidone | 13.00 |
| Sodium lauryl sulfate | 8.50 |
| Extra-granulate | |
| Amlodipine besylate | 13.90 |
| Croscarmellose sodium | 9.00 |
| Colloidal silicon dioxide | 3.50 |
| Magnesium stearate | 4.30 |
| Total | 450.00 |

TABLE 12

| Substance | mg/tab |
|---|---|
| Granulate | |
| Celecoxib | 200.00 |
| Mannitol | 137.10 |
| Croscarmellose sodium | 16.00 |
| Polyvinylpyrrolidone | 11.50 |
| Sodium lauryl sulfate | 7.50 |
| Extra-granulate | |
| Amlodipine besylate | 13.90 |
| Mannitol | 8.00 |
| Croscarmellose sodium | 8.00 |
| Colloidal silicon dioxide | 2.00 |
| Magnesium stearate | 4.00 |
| Total | 408.00 |

TABLE 13

| Substance | mg/tab |
|---|---|
| Granulate | |
| Celecoxib | 200.00 |
| Mannitol | 223.20 |
| Croscarmellose sodium | 20.00 |
| Polyvinylpyrrolidone | 14.50 |
| Sodium lauryl sulfate | 9.40 |
| Extra-granulate | |
| Amlodipine besylate | 13.90 |
| Croscarmellose sodium | 10.00 |
| Colloidal silicon dioxide | 4.00 |
| Magnesium stearate | 5.00 |
| Total | 500.00 |

TABLE 14

| Formulation No. | Tablet Thickness (mm) | Friability (%) | Average Hardness (N) |
|---|---|---|---|
| TABLE 1 | 5.60-5.64 | 0.2-0.3 | 83-87 |
| TABLE 2 | 5.73-5.84 | 0.1 | 82-85 |
| TABLE 3 | 5.20-5.25 | 0.0-0.1 | 78-86 |
| TABLE 4 | 5.67-5.73 | 0.0 | 88-93 |
| TABLE 5 | 5.52-5.59 | 0.1-0.2 | 87 |
| TABLE 6 | 5.73-5.78 | 0.2-0.3 | 83-91 |
| TABLE 7 | 5.40-5.46 | 0.2 | 93-97 |
| TABLE 8 | 5.57-5.59 | 0.3 | 86 |
| TABLE 9 | 6.41-6.43 | 0.0 | 86 |
| TABLE 10 | 6.38-6.65 | 0.2-0.3 | 68-76 |
| TABLE 11 | 6.19-6.26 | 0.2-0.3 | 98-119 |
| TABLE 12 | 5.48-5.51 | 0.3 | 115 |
| TABLE 13 | 6.65-6.97 | 0.0-0.3 | 77-110 |

Example 2

Stability of Compositions Containing Celecoxib and Amlodipine

In order to determine the effect of LOD % of the granules on the stability of the entire composition, two batches of acelecoxib and amlodipine composition as set forth in Table 2 above were prepared with different LOD % set points of the dry granules before admixture with the extra-granular material. Specifically, the LOD % of the granules of one batch ('batch A') was set to be in the higher LOD % range of 1.8-2.3% while the LOD % of the granules of the other batch ('batch B') was set to being the lower LOD % range of 0.5-1%. Stability of the batches was determined by placing the compositions in storage at 25° C. and 60% relative humidity (RH) and 40° C. and 75% relative humidity (RH) for 3 months. After storage, the different batches were tested for celecoxib release after 45 minutes and amlodipine release after 15 minutes at a 900 mL medium, pH 6.8 (containing SLS surfactant at about 0.5%), 100 rpm, Apparatus 2. The different batches were further tested for celecoxib and amlodipine assays and the levels of amlodipine USP related compound A, any unknown individual impurity, and total impurities. The results are detailed in Table 15.

TABLE 15

| Test | Batch A | Batch B |
|---|---|---|
| Celecoxib release | | |
| T = 0 | 94% | 84% |
| T = 3M at 25° C. & 60% RH | 98% | 82% |
| T = 3M at 45° C. & 75% RH | 97% | 81% |
| Amlodipine release | | |
| T = 0 | 81% | 97% |
| T = 3M at 25° C. & 60% RH | 78% | 96% |
| T = 3M at 45° C. & 75% RH | 73% | 95% |
| Celecoxib assay | | |
| T = 0 | 99.6% | 101.3% |
| T = 3M at 25° C. & 60% RH | 99.0% | 101.3% |
| T = 3M at 45° C. & 75% RH | 99.1% | 99.8% |
| Amlodipine assay | | |
| T = 0 | 98.8% | 95.0% |
| T = 3M at 25° C. & 60% RH | 97.8% | 95.3% |
| T = 3M at 45° C. & 75% RH | 95.2% | 100.2% |
| USP related compound A | | |
| T = 0 | <0.1% | <0.1% |
| T = 3M at 25° C. & 60% RH | <0.1% | <0.1% |
| T = 3M at 45° C. & 75% RH | 0.7% | <0.1% |
| Any unknown individual impurity | | |
| T = 0 | <0.1% | <0.1% |
| T = 3M at 25° C. & 60% RH | <0.1% | <0.1% |
| T = 3M at 45° C. & 75% RH | <0.1% | <0.1% |
| Total impurity | | |
| T = 0 | <0.1% | <0.1% |
| T = 3M at 25° C. & 60% RH | <0.1% | <0.1% |
| T = 3M at 45° C. & 75% RH | 0.7% | <0.1% |

As shown in Table 15, the comparative batches showed significantly different amlodipine release rates of a composition prepared from a granulate having LOD % at the higher range as compared to a composition prepared from a granulate having LOD % at the lower range. In particular, whereas the release of amlodipine at 15 minutes was 97% at T=0 and 95-96% after 3 months at storage for a composition prepared from a granulate having LOD % of 0.5-1%, the release of amlodipine from a composition prepared from a granulate having LOD % of 1.8-2.3% was 81% at T=0 and 73-78% after 3 months at storage. In addition, the impurity levels and, in particular, the levels of amlodipine USP related compound A after 3 months at 45° C. and 75% RH of a composition prepared from a granulate having LOD % of 1.8-2.3% was significantly higher (0.7%).

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

The invention claimed is:

1. A method for treating pain and/or hypertension, and ameliorating celecoxib-induced elevation of blood pressure in a subject, comprising providing to the subject a pharmaceutical composition comprising
   (i) an admixture comprising
      a dry granulate comprising celecoxib or a pharmaceutically acceptable salt, wherein said dry granulate has a loss on drying (LOD) % of about 2.5% or less, wherein said dry granulate does not include amlodipine; and
      an extragranulate comprising amlodipine or a pharmaceutically acceptable salt thereof admixed with the dry granulate; and
   (ii) one or more excipients selected from the group consisting of a diluent, a disintegrant, a surfactant, a binder, a glidant, a lubricant, and combinations thereof, wherein the amount of celecoxib is sufficient to cause elevation in blood pressure, and wherein the amount of amlodipine is sufficient to ameliorate blood pressure elevation.

2. The method of claim 1, wherein each of the dry granulate and the extragranulate includes at least one of the one or more excipients, and wherein the at least one of the one or more excipients in the dry granulate and the at least one of the one or more excipients in the extragranulate are the same or different.

3. The method of claim 1, wherein the one or more excipients includes a diluent selected from the group consisting lactose, sucrose, mannitol, sorbitol, calcium phosphate, cellulose, kaolin, sodium chloride, and starch.

4. The method of claim 1, wherein the one or more excipients includes a disintegrant selected from the group consisting of cross-linked sodium carboxymethyl cellulose (croscarmellose sodium), cross-linked polyvinylpyrrolidone (crospovidone), sodium starch glycolate, pregelatinized starch, calcium carboxymethyl cellulose, low substituted hydroxypropyl cellulose, and magnesium aluminum silicate.

5. The method of claim 1, wherein the one or more excipients includes a surfactant selected from the group consisting of stearyl triethanolamine, sodium lauryl sulfate, sodium taurocholate, laurylaminopropionic acid, lecithin, benzalkonium chloride, benzethonium chloride, glycerin monostearate, and polyvinyl alcohol.

6. The method of claim 1, wherein the one or more excipients includes a binder selected from the group consisting of polyvinylpyrrolidone (povidone; PVP), hydroxypropyl cellulose (HPC), hydroxypropylmethyl cellulose (HPMC), sodium alginate, alginic acid, guar gum, acacia gum, xanthan gum, carbopol, carboxymethyl cellulose, ethyl cellulose, maltodextrin, vinylpyrrolidone/vinyl acetate copolymer, microcrystalline cellulose, starch, and methyl cellulose.

7. The method of claim 1, wherein the one or more excipients includes a glidant selected from the group consisting of corn starch, colloidal silicon dioxide, silica anhydrous, and talc.

8. The method of claim 1, wherein the one or more excipients includes a lubricant selected from the group consisting of magnesium stearate, calcium stearate, oleic acid, caprylic acid, stearic acid, magnesium isovalerate, calcium laurate, magnesium palmitate, behenic acid, glyceryl behenate, glyceryl stearate, sodium stearyl fumarate, potassium stearyl fumarate, zinc stearate, sodium oleate, sodium stearate, sodium benzoate, sodium acetate, sodium chloride, talc, polyethylene glycol, and hydrogenated vegetable oil.

9. The method of claim 1, wherein the pharmaceutical composition is in the form of a tablet, a caplet, or a capsule.

10. The method of claim 1, wherein the dry granulate has LOD % in the range of from about 0.5% to about 2%.

11. The method of claim 1, wherein the dry granulate has LOD % in the range of from about 0.5% to about 1.5%.

12. The method of claim 1, wherein the pharmaceutical composition comprises 200 mg celecoxib and 2.5, 5, or 10 mg amlodipine.

13. The method of claim 1, wherein the pharmaceutically acceptable salt of amlodipine is amlodipine besylate.

14. The method of claim 1, wherein the dry granulate comprises celecoxib, a diluent, a disintegrant, a binder, and a surfactant; and wherein the extragranulate comprises amlodipine besylate, a diluent, a disintegrant, a glidant, and a lubricant.

15. A method for treating pain and/or hypertension, and ameliorating celecoxib-induced elevation of blood pressure in a subject, comprising providing to the subject a pharmaceutical composition comprising a combination of celecoxib and amlodipine, wherein the pharmaceutical composition is prepared from a wet granulation of celecoxib or a pharmaceutically acceptable salt thereof and one or more excipients to obtain a wet granulate, wherein said wet granulate does not include amlodipine, wherein the wet granulate was dried to obtain a dry granulate, wherein the dry granulate has a loss on drying (LOD) % of about 2.5% or less, wherein the dry granulate was admixed with an extragranulate comprising amlodipine or a pharmaceutically acceptable salt thereof and optionally one or more excipients, wherein the amount of celecoxib is sufficient to cause elevation in blood pressure, and wherein the amount of amlodipine is sufficient to ameliorate blood pressure elevation.

16. The method of claim 15, wherein the dry granulate has LOD % in the range of from about 0.5% to about 2%.

17. The method of claim 15, wherein the dry granulate has LOD % in the range of from about 0.5% to about 1.5%.

18. The method of claim 15, wherein the wet granulation was formed by dry mixing celecoxib or a pharmaceutically acceptable salt thereof and one or more excipients to obtain a dry mixture, and spraying the dry mixture with a granulation solution or suspension to obtain a wet granulate.

19. The method of claim 18, wherein the granulation solution or suspension comprises an aqueous medium.

20. The method of claim 18, wherein the granulation solution or suspension comprises an organic medium.

21. The method of claim 15, wherein the extragranulate comprises one or more excipients, and wherein the one or more excipients in the wet granulate and the one or more excipients in the extragranulate are the same or different selected from the group consisting of a diluent, a disintegrant, a surfactant, a binder, a glidant, a lubricant, and combinations thereof.

22. The method of claim 15, wherein the dry granulate was milled to produce a milled dry granulate prior to being admixed with the extragranulate.

23. The method of claim 15, wherein the pharmaceutical composition was compressed to obtain a tablet or a caplet.

24. The method of claim 15, wherein the subject has osteoarthritis.

* * * * *